United States Patent
Conlon et al.

(10) Patent No.: US 12,139,741 B2
(45) Date of Patent: *Nov. 12, 2024

(54) BIOCIDE COMPOSITIONS COMPATIBLE WITH ENZYME BIOSENSORS AND METHODS OF USE THEREOF

(71) Applicant: Instrumentation Laboratory Company, Bedford, MA (US)

(72) Inventors: Dennis Robert Conlon, Shirley, MA (US); Prasad Pamidi, Burlington, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/664,264

(22) Filed: Oct. 25, 2019

(65) Prior Publication Data

US 2021/0123084 A1 Apr. 29, 2021

(51) Int. Cl.
  *C12Q 1/18* (2006.01)
  *C12Q 1/34* (2006.01)
  *G01N 33/70* (2006.01)

(52) U.S. Cl.
  CPC .............. *C12Q 1/18* (2013.01); *C12Q 1/34* (2013.01); *G01N 33/70* (2013.01)

(58) Field of Classification Search
  None
  See application file for complete search history.

(56) References Cited

U.S. PATENT DOCUMENTS

| | | | |
|---|---|---|---|
| 2,585,501 A * | 2/1952 | Rusoff | A23C 19/11 426/303 |
| 2,728,704 A * | 12/1955 | Edds | C07D 499/00 424/114 |
| 3,689,646 A | 9/1972 | Sevag et al. | |
| 4,526,783 A | 7/1985 | Cole et al. | |
| 5,135,924 A | 8/1992 | Brandt et al. | |
| 5,202,427 A | 4/1993 | Umezawa et al. | |
| 5,283,005 A | 2/1994 | Nelson et al. | |
| 5,464,747 A | 11/1995 | Eisenbeis et al. | |
| 5,506,216 A | 4/1996 | Schmidt et al. | |
| 5,585,544 A * | 12/1996 | Cheney | A01H 13/00 435/430 |
| 5,741,663 A | 4/1998 | Russell | |
| 6,051,389 A | 4/2000 | Ahl et al. | |
| 6,071,392 A | 6/2000 | Yamamoto | |
| 6,368,847 B1 | 4/2002 | Line et al. | |
| 6,767,441 B1 | 7/2004 | Cai | |
| 6,841,527 B2 | 1/2005 | Mitra et al. | |
| 6,861,232 B2 | 3/2005 | Schaffar et al. | |
| 6,960,466 B2 | 11/2005 | Pamidi et al. | |
| 7,285,198 B2 | 10/2007 | Douglas | |
| 7,632,672 B2 | 12/2009 | Pamidi et al. | |
| 7,815,788 B2 | 10/2010 | Schaffar et al. | |
| 7,960,164 B2 | 6/2011 | Olstein | |
| 8,268,604 B2 | 9/2012 | Collier et al. | |
| 8,404,096 B2 | 3/2013 | Purvis et al. | |
| 8,426,192 B2 | 4/2013 | Pamidi et al. | |
| 8,466,345 B2 | 6/2013 | Martinell et al. | |
| 8,501,457 B2 | 8/2013 | Li et al. | |
| 9,029,118 B1 | 5/2015 | Olstein | |
| 9,487,811 B2 | 11/2016 | Zhao et al. | |
| 11,293,890 B2 | 4/2022 | Xu et al. | |
| 11,327,042 B2 | 5/2022 | Xu et al. | |
| 11,460,431 B2 | 10/2022 | Xu et al. | |
| 11,761,921 B2 | 9/2023 | Xu | |
| 2004/0163949 A1 | 8/2004 | Sorensen | |
| 2004/0211666 A1 | 10/2004 | Pamidi et al. | |
| 2004/0256227 A1 | 12/2004 | Shin et al. | |
| 2006/0094120 A1 * | 5/2006 | Clark | G01N 33/96 436/80 |
| 2006/0222564 A1 | 10/2006 | Dale et al. | |
| 2006/0275857 A1 | 12/2006 | Kjaer et al. | |
| 2006/0286625 A1 * | 12/2006 | McIlroy | C12N 1/20 435/253.6 |
| 2007/0034512 A1 | 2/2007 | Yamaoka | |
| 2007/0131548 A1 | 6/2007 | Winarta | |
| 2008/0173064 A1 | 7/2008 | Schaffar et al. | |
| 2008/0260763 A1 * | 10/2008 | Felgner | A61K 39/12 530/300 |
| 2010/0227345 A1 | 9/2010 | Lejuene et al. | |
| 2013/0186755 A1 | 7/2013 | Chu | |
| 2014/0224671 A1 | 8/2014 | Koide | |
| 2016/0054334 A1 * | 2/2016 | Biessen | C12Q 1/6883 435/7.1 |

(Continued)

FOREIGN PATENT DOCUMENTS

| | | | |
|---|---|---|---|
| CN | 103609425 B | * | 5/2015 |
| EP | 1825255 B1 | | 8/2011 |

(Continued)

OTHER PUBLICATIONS

Lin et al. J. Antimicrobial Therapy (1979) 5: 37-44 (Year: 1979).*
Wei et al. J. Microbiol. Immunol. Infection (2017) 50: 821-830 (Year: 2017).*
MacGowan et al. Clin. Microbial Infect. (1999) 5: 32-36 (Year: 1999).*
Shimizu et al. (Microbiol. Immunol. 1981) 25(8): 773-786 (Year: 1981).*
Names for Vantocil 1B from the Registry File on STN downloaded Aug. 14, 2021 (Year: 2021).*

(Continued)

*Primary Examiner* — Sean C. Barron (74) *Attorney, Agent, or Firm* — ArentFox Schiff LLP (57) ABSTRACT

The present disclosure relates to biocide compositions compatible with enzyme biosensors and methods for using same. More particularly, the disclosure relates to biocide compositions compatible with enzymes used for measuring creatine and creatinine levels.

29 Claims, 6 Drawing Sheets

(56) References Cited

U.S. PATENT DOCUMENTS

| | | | |
|---|---|---|---|
| 2017/0007616 A1* | 1/2017 | Gardner | A61K 31/5383 |
| 2017/0107535 A1* | 4/2017 | Narva | C07K 14/43563 |
| 2017/0254771 A1 | 9/2017 | Balasubramanian et al. | |
| 2017/0283771 A1* | 10/2017 | Telfer | C12N 5/0037 |
| 2018/0187151 A1* | 7/2018 | Guillonneau | A61P 37/06 |
| 2020/0319210 A1 | 10/2020 | Xu et al. | |
| 2022/0154244 A1 | 5/2022 | Conlon et al. | |
| 2022/0187234 A1 | 6/2022 | Xu et al. | |

FOREIGN PATENT DOCUMENTS

| | | | | |
|---|---|---|---|---|
| EP | 1753872 B1 | 1/2014 | | |
| EP | 3397162 B1 | 9/2023 | | |
| GB | 2122900 A | * | 1/1984 | A61L 2/18 |
| JP | H09-504179 A | 4/1997 | | |
| JP | 2000-507457 A | 6/2000 | | |
| JP | 2003-533679 A | 11/2003 | | |
| JP | 2004-528579 A | 9/2004 | | |
| JP | 2005-501254 A | 1/2005 | | |
| JP | 2006-507498 A | 3/2006 | | |
| JP | 2008-502921 A | 1/2008 | | |
| JP | 2008-541104 A | 11/2008 | | |
| JP | 2011-508221 A | 3/2011 | | |
| JP | 2014-153243 A | 8/2014 | | |
| WO | 1998021356 A1 | 5/1998 | | |
| WO | 2003019171 A1 | 3/2003 | | |
| WO | 2004053483 A2 | 6/2004 | | |
| WO | 2005052596 A1 | 6/2005 | | |
| WO | 2006122553 A1 | 11/2006 | | |
| WO | 2008028011 A2 | 3/2008 | | |
| WO | 2009053370 A1 | 4/2009 | | |
| WO | 2009082699 A1 | 7/2009 | | |
| WO | 2016096725 A1 | 6/2016 | | |
| WO | 2016135136 A1 | 9/2016 | | |
| WO | 2017117565 A1 | 11/2018 | | |

OTHER PUBLICATIONS

Young et al. Plant Sci. Lett. (1984) 34: 203-209 (Year: 1984).*
Barnet et al. Biological control (2017) 113: 45-57 (Year: 2017).*
Brooke et al. J. Med. Microbiol. (2003) 52: 509-513 (Year: 2003).*
Machine translation of CN 103609425 B (published May 27, 2015) downloaded from Innovation Plus on Apr. 22, 2022 (Year: 2015).*
Kwa et al. Pharmacokinetics of Polymyxin B in a Patient With Renal Insufficiency: A Case Report. Clin Infect Dis (2011), 52(10), 1280-1281. (Year: 2011).*
Cooper et al. Creatine supplementation with specific view to exercise/sports performance: an update. Journal of the International Society of Sports Nutrition (2012), 9(33), 11 page reprint. (Year: 2012).*
Yoshimoto et al., crystal structures of creatininase reveal the substrate binding site and provide an insight into the catalytic mechanism, Journal of Molecular Biology, vol. 337, No. 2, Mar. 19, 2004, pp. 399-416.
International Search Report and Written Opinion issued in corresponding PCT application No. PCT/US2019/058009, dated Sep. 14, 2020, (20 pages).
Invitation to Pay Additional Fees issued in corresponding PCT application No. PCT/US2019/058009, dated Jul. 16, 2020, (16 pages).
International Preliminary Report on Patentability for International Patent Application No. PCT/US2019/058009, dated May 5, 2022, 14 pages.
Conway et al., "Layer-by-layer design and optimization of xerogel-based amperometric first generation biosensors for uric acid," Journal of Electroanalytical Chemistry, vol. 775, pp. 135-145 (2016), 37 pages.
"FDA updates warnings for fluoroquinolone antibiotics," U.S. Food & Drug Administration, FDA News Release [online] URL:https://www.fda.gov/news-events/press-announcements/fda-updates-warnings-fluoroquinolone-antibiotics (Jul. 26, 2016), 2 pages.
"Hydromed D Series," AdvanSource Biomaterials, (Apr. 16, 2010) [online] Retrieved from the Internet <URL: http://www.advbiomaterials.com/products/hydrophilic/HydroMed. pdf> [retrieved on Sep. 20, 2019], 3 pages.
"Hydro Thane ™," AdvanSource Biomaterials, (Jun. 21, 2011) [online] Retrieved from the Internet <URL: http://www. advbiomaterials.com/pdf/HydroThane%20Factsheet.pdf> [retrieved on Sep. 19, 2019], 3 pages.
Magalhaes et al., "Urea potentiometric biosensor based on urease immobmzed on chitosan membranes," Talanta, vol. 47, pp. 183-191 (1998), 9 pages.
Mohapatra et al., "Polymyxins, the last-resort antibiotics: Mode of action, resistance emergence, and potential solutions," J. Biosci 46:85 (2021), 18 pages.
Monošík et al., "Application of electrochemical biosensors in clinical diagnosis," Journal of Clinical Laboratory Analysis, vol. 26(1), pp. 22-34 (2012), 13 pages.
Nichols et al., "The effect of nitric oxide surface flux on the foreign body response to subcutaneous implants," Biomaterials, vol. 33, No. 27, pp. 6305-6312 (2012), 21 pages.
Russo et al., "Charge accumulation in electron cryomicroscopy," Ultramicroscopy, vol. 187, pp. 43-49, DOI: 10.1016/j.ultramic.2018.01.009 (2018), 15 pages.
Tjell et al., "Diffusion rate of hydrogen peroxide through water-swelled polyurethane membranes," Sensing and Bio-Sensing Research, vol. 21, No. 27, pp. 35-39 (2018), 5 pages.
Non-Final Office Action in U.S. Appl. No. 17/591,296 dated Dec. 22, 2023, 8 pages.
First Office Action in Chinese Application No. 201980042702.7 dated Mar. 30, 2024 [with English translation], 14 pages.
Final Office Action in U.S. Appl. No. 17/680,487 dated Apr. 8, 2024, 42 pages.
Cicerone et al., "Stabilization of Proteins in Solid Form", Advanced Drug Delivery Reviews, vol. 93, pp. 14-24 (2015), 28 pages.
Examiner Requisition in Canadian Application No. 3,104,896 dated Mar. 21, 2024, 6 pages.

* cited by examiner

BIOCIDE COMPOSITIONS COMPATIBLE WITH ENZYME BIOSENSORS AND METHODS OF USE THEREOF

FIELD OF THE DISCLOSURE

The disclosure relates to biocide compositions compatible with enzyme biosensors and methods for using same. More particularly, the disclosure relates to biocide compositions compatible with enzymes used for measuring creatine and creatinine levels.

BACKGROUND OF THE DISCLOSURE

Whole blood critical care analyzers (WBCCAs) play an essential role in the management of critically ill patients by providing rapid therapeutic turnaround times at point of care sites. Biocides are a critical component of WBCCA reagents that inhibits the effects of microbial metabolism on blood analysis results. For example, normal oxygen content in human blood is very low, and any consumption of oxygen by bacteria in the calibration solution causes a significant error in reported oxygen levels. WBCCAs have also evolved to include electrochemical biosensor based measurement of metabolites such as, for example, creatinine/creatine levels in a sample (e.g., a patient's blood), which is an important indication of renal function. Current creatinine sensors may include an enzymatic biosensor containing three enzymes—creatininase, creatinase, and sarcosine oxidase—that catalyze the production of glycine, formaldehyde, and hydrogen peroxide from creatinine and water so that the final reaction product of hydrogen peroxide ($H_2O_2$) may then be electrochemically oxidized to measure creatinine and/or creatine levels in the sample (e.g., a patient's blood). An important consideration in the design and use of WBCCA enzymatic biosensors is that the catalytic activity of the biosensor enzymes is dependent on multiple parameters, including solution conditions such as, for example, pH, temperature, the levels of metabolites such as oxygen, and the like. Additionally, such enzymes are also greatly affected by the presence of any inhibitors. Unfortunately, enzymes that are used in enzymatic biosensors are frequently either inhibited or inactivated by current biocides. For example, creatinine biosensors are an example of an important enzymatic biosensor that is inactivated by current biocides. Accordingly, there is a need for biocide compositions that are compatible with enzyme biosensors.

SUMMARY OF THE DISCLOSURE

The present disclosure provides efficacious biocidal reagents that do not inhibit or prevent the function of whole blood critical care analyzers (WBCCAs). In particular, the present disclosure provides some efficacious biocides that do not inhibit or prevent WBCCAs having sensor function or enzymatic biosensor function. Additionally, the present disclosure provides biocidal reagents with a molecular weight (MW) greater than 320 that do not inhibit or prevent enzymatic biosensor function. Additionally, the present disclosure provides some efficacious biocides that do not inhibit or prevent enzymatic biosensor function. Exemplary efficacious biocidal reagents that do not inhibit or prevent the function of enzymatic biosensors include, but are not limited to, Levofloxacin, Carbenicillin disodium, Spectinomycin, Piperacillin, Ceftazidime, Streptomycin, Polymyxin B, Polymyxin E, Sulfanilamide, Sulfathiazole sodium, Sulfadimethoxine, Vantocil™ IB (polyhexamethylene biguanide hydrochloride), and the like. Advantageously, the biocidal reagents disclosed herein are able to effectively neutralize or destroy harmful organisms (e.g., bacteria, fungi, and the like) without inhibiting or preventing the function of an enzymatic biosensor. The present disclosure also provides methods of identifying biocides that are compatible with any of a variety of enzymatic biosensors. Furthermore, the present disclosure also provides methods of using the disclosed biocides. The compositions and methods provided herein are important because they allow whole blood critical care analyzers (WBCCAs) having enzymatic biosensors to efficiently perform readings on biological samples in the presence of biocidal reagents that do not negatively impact the function of the enzymatic biosensors.

In an aspect, the present disclosure provides a method for preserving function of a sensor that includes the steps of: adding one or more sensor compatible biocides (SCBs) to a solution; and measuring with the sensor a concentration of one or more analytes. In some embodiments, the sensor may be a biosensor, a gas sensor, an ion selective electrode, or a photometric sensor. In some embodiments, the biosensor is an enzyme biosensor. In some embodiments, the enzyme biosensor may be a creatinine sensor, a creatine sensor, or a combination thereof.

In some embodiments, the SCB is an antibiotic having a molecular weight greater than about 320 g/mol.

In some embodiments, the SCB is a polymyxin selected from the group consisting of Polymyxin B, Polymyxin E, and combinations thereof.

In some embodiments, the SCB is Polymyxin B.

In some embodiments, the SCB is fluoroquinolone.

In some embodiments, the SCB contains a sulfone group.

In some embodiments, the solution is a biological sample, a Process Control Solution (PCS), a calibration solution, a quality control solution, a conditioning solution, or a wash solution.

In some embodiments, the SCB is a Beta-lactam antibiotic selected from the group consisting of: amoxycillin, ampicillin, carbenicillin, cefazolin, cefepime, cefoxitin, ceftazidime, clavulanic acid, imipenem, oxacillin, penicillin, and piperacillin.

In some embodiments, the SCB includes at least one Beta-lactam antibiotic and a polymyxin.

In some embodiments, the solution further includes a beta-lactamase inhibitor.

In some embodiments, the SCB includes a polymyxin and a fluoroquinolone.

In one aspect, the disclosure provides a method of identifying an Enzyme Biosensor Compatible Biocide (EBCB) for an enzyme biosensor that includes the steps of: measuring stable enzyme biosensor activity for an enzyme biosensor in solution for a period of time; adding one or more biocidal agents to the solution containing the enzyme biosensor; determining antimicrobial efficacy of the biocidal agent in the solution; measuring the enzyme biosensor activity in response to the one or more biocidal agents for an additional period of time, wherein the enzyme biosensor activity is assessed based on an enzyme slope; and selecting, based on the enzyme slope, the EBCB.

In some embodiments, the biocidal agent is one or more antibiotics having a molecular weight greater than about 350 g/mol.

In some embodiments, the EBCB contains a sulfone group.

In some embodiments, the EBCB is a Beta-lactam antibiotic.

In some embodiments, the WBCCA sensor is a gas sensor, an ion selective electrode, a photometric sensor, and the like.

In some embodiments, the WBCCA sensor is an enzyme biosensor, optionally a Creatinine/Creatine Sensor.

In one aspect, the disclosure provides a composition, including one or more enzyme biosensor compatible biocides (EBCBs) selected from the group consisting of Levofloxacin, Carbenicillin disodium, Spectinomycin, Piperacillin, Ceftazidime, Streptomycin, Polymyxin B, Polymyxin E, Sulfanilamide, Sulfathiazole sodium, Sulfadimethoxine, and Vantocil™ IB.

In one aspect, the disclosure provides a composition, including: a first enzyme biosensor compatible biocide (EBCB); and a second EBCBs.

In some embodiments, the first EBCB is selected from the group consisting of Levofloxacin, Carbenicillin disodium, Spectinomycin, Piperacillin, Ceftazidime, Streptomycin, Polymyxin B, Polymyxin E, Sulfanilamide, Sulfathiazole sodium, Sulfadimethoxine, and Vantocil™ IB.

In some embodiments, the second EBCB is selected from the group consisting of Levofloxacin, Carbenicillin disodium, Spectinomycin, Piperacillin, Ceftazidime, Streptomycin, Polymyxin B, Polymyxin E, Sulfanilamide, Sulfathiazole sodium, Sulfadimethoxine, and Vantocil™ IB.

In some embodiments, the first EBCB or second EBCB is a penicillin selected from the group consisting of amoxycillin, carbenicillin and benzyl penicillin.

In some embodiments, the penicillin is at a concentration of about 12.5 to about 500 μg/ml.

In some embodiments, the first EBCB is carbenicillin at a concentration of about 5 to about 800 μg/ml and the second EBCB is nitrofurantoin at a concentration of about 1 to about 200 μg/mL.

In some embodiments, the first EBCB or second EBCB is about 15 to about 1500 mg/L spectinomycin.

In some embodiments, the first EBCB or second EBCB is about 10 to about 500 mg/L of ceftazidime.

In some embodiments, the first EBCB or second EBCB is about 10-500 mM streptomycin.

In some embodiments, the first EBCB or second EBCB is about 20 to 100 mg/L polymyxin B.

In some embodiments, the first EBCB or second EBCB is about 20 to 100 mg/L polymyxin E.

In some embodiments, the first EBCB or second EBCB is Vantocil™ IB in a w/v of 0.1-0.5% in aqueous solution.

In some embodiments, the first EBCB is colistin and the second EBCB is levofloxacin.

Definitions

By "control" or "reference" is meant a standard of comparison. In one aspect, as used herein, "changed as compared to a control" sample or subject is understood as having a level that is statistically different than a sample from a normal, untreated, or control sample. Control samples include, for example, creatine solutions, creatinine solutions, and the like. Methods to select and test control samples are within the ability of those in the art. Determination of statistical significance is within the ability of those skilled in the art, e.g., the number of standard deviations from the mean that constitute a positive result.

As used herein, "creatine (a.k.a., 2-[Carbamimidoyl (methyl)amino]acetic acid, N-Carbamimidoyl-N-methylglycine, or Methylguanidoacetic acid)" refers to an organic compound that produce energy for the cells through the recycling of adenosine triphosphate (ATP) by converting adenosine diphosphate (ADP) back to ATP by donating phosphate groups. Creatine has the following chemical structure:

2-[Carbamimidoyl(methyl)amino]acetic acid

As used herein, "creatinine" refers to the enzymatic breakdown by-product of creatine, and is generally found in two major tautomeric forms, which are shown below.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed. Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Where applicable or not specifically disclaimed, any one of the embodiments described herein is contemplated to be able to combine with any other one or more embodiments, even though the embodiments are described under different aspects of the disclosure. For example, it is expressly contemplated within the scope of the disclosure that efficacious biocides may be used singly or as combinations of two or more efficacious biocides.

These and other embodiments are disclosed and/or encompassed by, the following detailed description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIGS. 1A-1C show the crystal structure reconstructions of the enzymes present in a creatininase sensor.

FIGS. 2A-2B show plots of creatinine and creatine slopes over time in the presence of either MIT or polymyxin B, respectively.

DETAILED DESCRIPTION OF THE DISCLOSURE

The present disclosure is based, at least in part, on the unexpected discovery that biocidal reagents that fall within particular molecular weight ranges do not inhibit or prevent the function of enzymes with an enzymatic biosensor. In particular, the present disclosure provides the unexpected and surprising discovery that biocidal reagents having a molecular weight (MW) greater than 320 do not inhibit or prevent the function of enzymes within an enzymatic biosensor. The present disclosure provides a number of specific efficacious biocidal reagents that do not inhibit or prevent the function of enzymes within an enzymatic biosensor that include, but are not limited to, Levofloxacin, Carbenicillin disodium, Spectinomycin, Piperacillin, Ceftazidime, Streptomycin, Polymyxin B, Polymyxin E, Sulfanilamide, Sulfathiazole sodium, Sulfadimethoxine, Vantocil™ IB, and the like. Advantageously, the biocidal reagents disclosed herein are able to effectively neutralize or destroy harmful organisms (e.g., bacteria, fungi, and the like) without inhibiting or preventing the function of an enzymatic biosensor. The present disclosure also provides methods of identifying efficacious biocides that are specific to, and compatible with, any of a variety of enzymatic biosensors. Furthermore, the present disclosure also provides methods of using the disclosed biocides. The compositions and methods provided herein are important because they allow whole blood critical care analyzers (WBCCAs) having enzyme-based biosensors to efficiently perform readings on biological samples in the presence of biocidal reagents that do not negatively impact the function of the enzymatic biosensors.

Overview

Historically, WBCCAs were used only to measure blood gases, electrolytes, and CO-Oximetry, which made it relatively straightforward to select a biocide that was compatible for use in these assays. However, when the assay repertoire of WBCCAs was expanded to include metabolites such as glucose, lactate, creatinine, creatine, and the like, it became very difficult to identify biocides that were compatible with these assays because they generally include enzyme-based biosensors, and the enzymes that are incorporated into these biosensors are inactivated by most biocidal agents. It has been a significant challenge in the prior art to identify biocidal reagents that are powerful enough to kill all likely bacteria, yeasts and fungi without simultaneously deactivating the enzymes that are incorporated into enzymatic biosensors. As an example, one prior art solution incorporated by medical manufacturers of critical care analyzers was to change from using chlorinated isothiazolinones (e.g., ProClin 300) to non-chlorinated isothiazolinones (e.g., methyl isothiazolinone (MIT)). Disadvantageously, non-chlorinated isothiazolinones have a higher minimal inhibitory concentration (MIC) that requires a higher concentration to meet minimum bactericidal requirements, and results in a concomitant increase in reagent costs.

Whole blood based blood gas analyzers are more susceptible to microbial growth than most other types of clinical analyzers because their calibrators maintain a stable level of oxygen, which is reported as the partial pressure $pO_2$. This presents a significant problem because $pO_2$ values reported for patients often sound like a large quantity, e.g., 90 mmHg is a normal $pO_2$ result, which is similar to normal chloride results, 95 mmol/L, and much greater than normal ionized calcium, about 1.1-1.2 mmol/L; however, these numerical values are deceptive because it is moles and millimoles that matter, and due to the poor solubility of oxygen in water, normal oxygen content in human blood is on the order of only 0.1 mmol/L. Given that calibrators are expected to be stable within 1% if possible, a loss of only 0.001 millimole or 1 micromole of oxygen can make the oxygen channel on an analyzer less accurate than ideal. As a result, bacterial contamination within an analyzer can produce significant measurement errors. For example, if a given colony of bacteria consumed 10 micromoles of both oxygen and glucose (e.g., within a calibration solution), then the analyzer would report $pO_2$ with a significant error of about 10%, whereas the error in the glucose measurement would be proportionally much less significant, for example, a reduction from about 5.00 mmol/L to 4.99 mmol/L, which is relatively insignificant.

The problem of finding an efficacious biocide was exacerbated by the use of a different class of enzymes that were needed for other metabolites, such as creatinine and urea or blood urea nitrogen (BUN). Whereas glucose and lactate were most commonly measured with glucose oxidase and lactate oxidase respectively, creatinine was measured with two hydrolase class enzymes (e.g., creatininase and creatinase) and sarcosine oxidase. Unfortunately, some of these enzymes, e.g. creatininase, are inactivated by prior art biocides.

Creatininase, also known as creatinine amidohydrolase or creatinine hydrolase, is a $Zn^{2+}$-ion dependent hexamer that catalyzes the hydrolysis of creatinine to creatine. Creatinase, also known as creatine aminohydrolase, catalyzes the hydrolysis of creatine to sarcosine and urea. Sarcosine oxidase requires FAD (flavin adenine dinucleotide) and catalyzes the oxidative demethylation of sarcosine (N-methylglycine) to glycine.

Current creatinine sensors in a creatine/creatinine system (e.g., GEM PAK cartridge) include an enzymatic biosensor containing these three enzymes, which are immobilized on the surface of a platinum electrode. The creatinine detection system is based on the following three enzyme cascade reaction (Rx):

The product hydrogen peroxide ($H_2O_2$) is then electrochemically oxidized on the platinum electrode under the constant polarization potential, and the current signal is proportional to the analyte concentration.

The presence of creatine in clinical samples necessitates an additional sensor for creatine measurement to correct for the creatine response of the creatinine sensor. The creatine sensor includes only reactions (2) and (3) of the above enzyme cascade reactions.

Both the creatine and creatinine sensors have a diffusion control membrane (also referred to as an outer membrane) on top of the enzyme layers. The diffusion control membrane limits the flux of creatinine and creatine substrates entering the enzyme layer to ensure that the signals generated by the hydrogen peroxide are proportional to the substrate concentrations of the sample.

Calibration systems for a creatine sensor or biosensor may involve a 2-point calibration based on the following equation:

$$\Delta I2 = [CR\_CS2] * Slope \quad (Eq.\ 1)$$

ΔI2 is a current signal measured on the creatine sensor in a first calibration solution (CS2). [CR_CS2] is the concentration of creatine in the first calibration solution (CS2). CS2 may have a known concentration of creatine (CR_CS2), a known concentration of creatinine (CREA_CS2), and a stable ratio of creatine to creatinine, which makes it possible to establish a creatine sensor sensitivity (Slope) for the creatine sensor.

According to the techniques herein, a calibration system for a creatinine sensor or biosensor may implement a 3-point calibration methodology. As the creatinine sensor provides readings of both creatinine and creatine in biological samples or calibration solutions containing both analytes, the sensitivities of the creatinine sensor to creatinine (Slope1) or creatine (Slope2) may be determined according to the disclosure, as defined below, from equations 2-5 below. The disclosure provides that two calibration solutions with distinct ratios of creatine/creatinine may be used for the 3-point calibration method.

3-point creatinine sensor calibration equations:

$$\Delta I2' = [CREA\_CS2] * Slope1 + [CR\_CS2] * Slope2 \quad (Eq.\ 2)$$

$$\Delta I3' = [CREA\_CS3] * Slope1 + [CR\_CS3] * Slope2 \quad (Eq.\ 3)$$

ΔI2' and ΔI3' are current signals measured on creatinine sensor in a first calibration solutions (CS2) and a second calibration solution (CS3), respectively. CS3 may have an initial known creatine concentration (CR_CS3), an initial known creatinine concentration (CREA_CS3) and an unstable ratio of creatine to creatinine.

[CREA_CS2], [CREA_CS3], [CR_CS2] and [CR_CS3] represent the initial known concentrations of creatinine and creatine in calibration solutions CS2 and CS3, respectively. The sensitivity of the creatinine sensor for creatinine and creatine, Slope1 (sensor sensitivity to creatinine) and Slope2 (sensor sensitivity to creatine), can be derived from Eq. 2 and 3:

$$Slope1 = ([CR\_CS3] * \Delta I2' - [CR\_CS2] * \Delta I3') / ([Creat\_CS2] * [CR\_CS3] - [Creat\_CS3] * [CR\_CS2]) \ pA/mg/dL \quad (Eq.\ 4)$$

$$Slope2 = ([CREA\_CS2] * \Delta I3' - [CREA\_CS3] * \Delta I2') / ([Creat\_CS2] * [CR\_CS3] - [Creat\_CS3] * [CR\_CS2]) pA/mg/dL \quad (Eq.\ 5)$$

Additionally, to further complicate matters, the few biocides identified to date that are compatible with glucose and lactate oxidase enzymes have been found to be incompatible with creatininase, creatinase and sarcosine oxidase, which are generally used together. In particular, MIT, which is a commonly used biocide, causes rapid inactivation of creatininase, and creatinase. The difficulty associated with identifying biocides that are compatible with proteins such as enzymes or antibodies is discussed in U.S. Pat. No. 5,506,216, which notes that proteins can become denatured by such substances. U.S. Pat. No. 5,506,216 identified several biocidal agents including o-phenylphenol, Densil P [dithio-2,2'-bis(benzmethylamide)], [1,2-benzisothiazolin-3-thion] (Proxel), methylenebisthiocyanate, cyanate, hydroxyquinoline, Carbendazim [-methoxycarbonylamino-benzimidazol] and Dazomet[3,5-dimethyltetrahydro-1,3,5-thiodiazin-2-thion] and found that these agents could function as biocides that do not interact with proteins, but only if they were complexed with cyclodextrins. Consistent with these, few, if any, of these biocides are compatible with creatininase, creatinase and sarcosine oxidase based sensors.

Without wishing to be bound by theory, the creatininase enzyme biosensor active site consists of a narrow, hydrophobic cleft (Yoshimoto et al., 2004. Journal of Molecular Biology), and it is believed that binding of the creatine substrate to the creatininase enzyme may be prevented by denaturation of the enzyme by small, non-polar molecules such as occur in the biocide compositions disclosed herein.

In embodiments, a biocide composition compatible with the enzyme biosensors is a combination of sulfa drugs with another sulfa drug (see e.g., U.S. Pat. No. 9,029,118), or any other compatible biocide disclosed herein. In embodiments, the sulfa drug(s) may be present at a concentration of from about 0.05 g/L to about 20 g/L, about 0.3 g/L to about 10 g/L, about 0.3 g/L to about 5 g/L, and the like. It is contemplated within the scope of the disclosure that a biocide composition compatible with the enzyme biosensors may be a combination of sulfa drugs with any other of the compounds disclosed herein.

In embodiments, a biocide composition compatible with the enzyme biosensors is a combination of between about 100 to about 1,000 micrograms per milliliter of sulfathiazole and between about 20 to about 2,000 micrograms per milliliter of quinacrine hydrochloride (see e.g., U.S. Pat. No. 3,689,646).

In an embodiment, a biocide composition compatible with enzyme biosensors is a combination of sulfadimethoxine and ormetoprim in a weight ratio of sulfadimethoxine to ormetoprim of 5:1 (see e.g., U.S. Pat. No. 5,135,924).

In an embodiment, a biocide composition compatible with enzyme biosensors is about 125 to about 1,000 µg/ml of the penicillins (e.g., amoxycillin, carbenicillin, benzyl penicillin, piperacillin, ceftazidime, and the like) and between about 5 and 500 µg/ml of clavulanic acid (see e.g., U.S. Pat. No. 4,526,783). In some embodiments, the penicillin is carbenicillin.

In an embodiment, a biocide composition compatible with enzyme biosensors may include carbenicillin at a concentration of between about 100 and about 1,000 µg/ml and nitrofurantoin at a concentration of between about 100 and about 500 µg/mL (see e.g., U.S. Pat. No. 5,741,663) In embodiments, a biocide composition compatible with enzyme biosensors may include carbenicillin at a concentration of about 200 µg/mL a concentration of nitrofurantoin of about 100 µg/mL.

In an embodiment, a biocide composition compatible with enzyme biosensors may include about 100 mg/L to about 1,000 mg/L spectinomycin or streptomycin (see e.g., U.S. Pat. No. 8,466,345). In an embodiment, a biocide composition compatible with enzyme biosensors may include about 300 mg/L spectinomycin or streptomycin.

In an embodiment, a biocide composition compatible with enzyme biosensors may include between about 100 and about 1,000 µg/ml of ceftazidime (U.S. Pat. No. 8,501,457).

In an embodiment, a biocide composition compatible with enzyme biosensors may include between about 50 µg/ml and about 1,000 µg/ml of streptomycin (U.S. Pat. No. 5,202,427). In an embodiment, a biocide composition compatible with enzyme biosensors may include about 100 µg/ml of streptomycin In an embodiment, a biocide composition compatible with enzyme biosensors is about 1 and about 100 ppm for polymyxin B (U.S. Pat. No. 5,283,005).

In an embodiment, a biocide composition compatible with enzyme biosensors includes about 0.35 mg/L of polymyxin B (U.S. Pat. No. 6,368,847).

In an embodiment, a biocide composition compatible with enzyme biosensors may include polymyxin E (CAS No. 1066-17-7) at a concentration of between about 5 mg/L and about 200 mg/L (U.S. Pat. No. 7,960,164). In an embodiment, a biocide composition compatible with enzyme biosensors may include polymyxin E (CAS No. 1066-17-7) at a concentration of about 10 mg/L, about 15 mg/L, about 20 mg/L, about 25 mg/L, about 30 mg/L, about 35 mg/L, about 40 mg/L, about 45 mg/L, or about 50 mg/L.

In an embodiment, a biocide composition compatible with enzyme biosensors is Vantocil™ IB in a w/v of 0.1-0.5% in aqueous solution (U.S. Pat. No. 6,841,527).

Kits or Analyzer Cartridges

The instant disclosure also provides kits containing agents of this disclosure for use in the methods of the present disclosure. Kits of the instant disclosure may include one or more containers comprising one or more biocidal agents in one or more solutions (e.g., Process Control Solutions (PCS) including, but not limited to, PCS-A, PCS-B, PCS-C, PSC-D, and the like). Exemplary containers may include bags, glass ampules (e.g., sold as quality control solutions), and the like including solutions for calibrating and/or measuring a creatine and/or creatinine via enzymatic biosensor(s). In some embodiments, the kits further include instructions for use in accordance with the methods of this disclosure. In some embodiments, these instructions comprise a description of how to apply the biocide agents/solutions to a WBCCA according to any of the methods of the disclosure.

In some embodiments, the instructions comprise a description of how to install and calibrate a measuring system in the presence of a biocidal reagent as disclosed herein.

The instructions generally include information as to biocide reagent/solution concentration, reagent/solution ratio, shelf life, etc. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the reagents/solutions may be used to calibrate any of a variety of creatine and/or creatinine sensor(s) for use in a measuring system as described herein. Instructions may be provided for practicing any of the methods described herein, for example, to install and calibrate a measuring system.

The kits of this disclosure are in suitable packaging. Suitable packaging includes, but is not limited to, vials, ampules, bottles, carboys, jars, flexible packaging (e.g., sealed Mylar or plastic bags), foil laminate bags, and the like. Also contemplated are packages for use in combination with a specific device, such as GEM Premier whole blood analyzer family (Instrumentation Laboratory, Bedford, MA). In certain embodiments, at least one active agent in the reagent or solution includes, but is not limited to, Levofloxacin, Carbenicillin disodium, Spectinomycin, Piperacillin, Ceftazidime, Streptomycin, Polymyxin B, Polymyxin E, Sulfanilamide, Sulfathiazole sodium, Sulfadimethoxine, Vantocil™ IB, and the like.

Kits may optionally provide additional components such as buffers and interpretive information. Normally, the kit comprises a container and a label or package insert(s) on or associated with the container.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

EXAMPLES

The present disclosure is further illustrated by the following examples, which should not be construed as limiting. The contents of all references and published patents and patent applications cited throughout the application are hereby incorporated by reference. Those skilled in the art will recognize that the disclosure may be practiced with variations on the disclosed structures, materials, compositions and methods, and such variations are regarded as within the scope of the disclosure.

Example 1: Large Molecular Weight Biocides do not Inhibit or Inactivate Enzyme Biosensors The present disclosure discovered that Polymyxin B and Polymyxin E (aka, Colistin Sulfate) were compatible with a ChemSTAT creatinine sensor that utilized two hydrolase class enzymes (e.g., creatininase and creatinase) and sarcosine oxidase to measure creatinine. When included in Process Control Solutions (PCS) at a concentration sufficient to kill microbes (e.g., bacteria, in particular gram negative rods including various strains of *Pseudomonas*), the slope of the sensor remained high enough over 21 days to continually allow accurate measurement of creatinine in human blood and aqueous control solutions even at the upper end of the linear range where reduced enzyme activity could result in low recovery of substrate. It was surprising and unexpected to find a biocide that did not reduce the slope of this enzyme sensor to the point where it did not meet performance claims or more often, reduced the slope to zero.

Figure 1A:
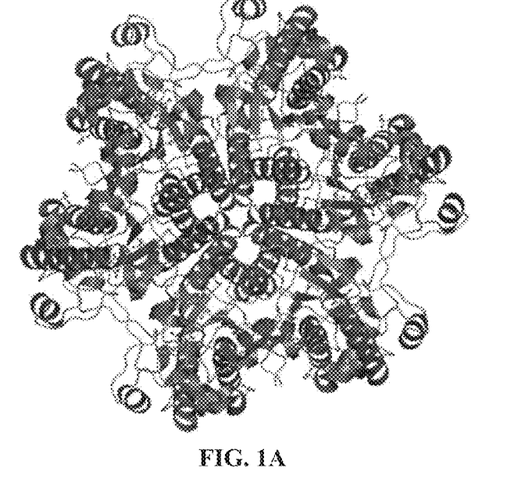
FIG. 1A is a ribbon diagram showing the quaternary structure of the creatininase hexamer as known in the prior art.
Figure 1B:
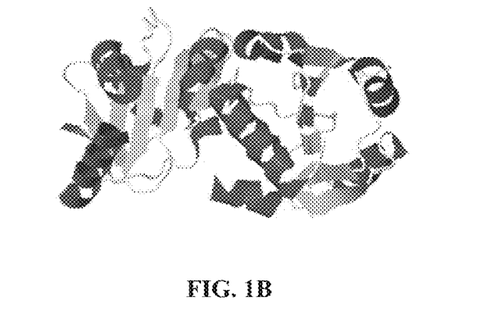
FIG. 1B is a ribbon diagram showing the tertiary structure of the creatinase N-terminal domain as known in the prior art.
Figure 1C:
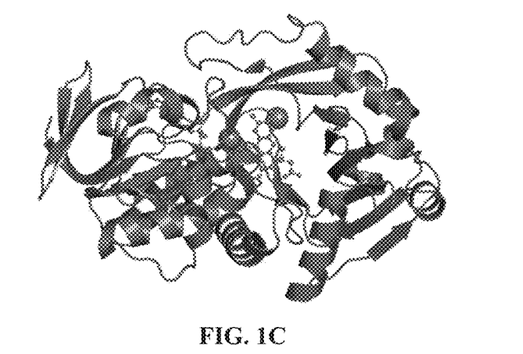
FIG. 1C is a ribbon diagram showing the tertiary structure of sarcosine oxidase as known in the prior art.
Figure 2A:
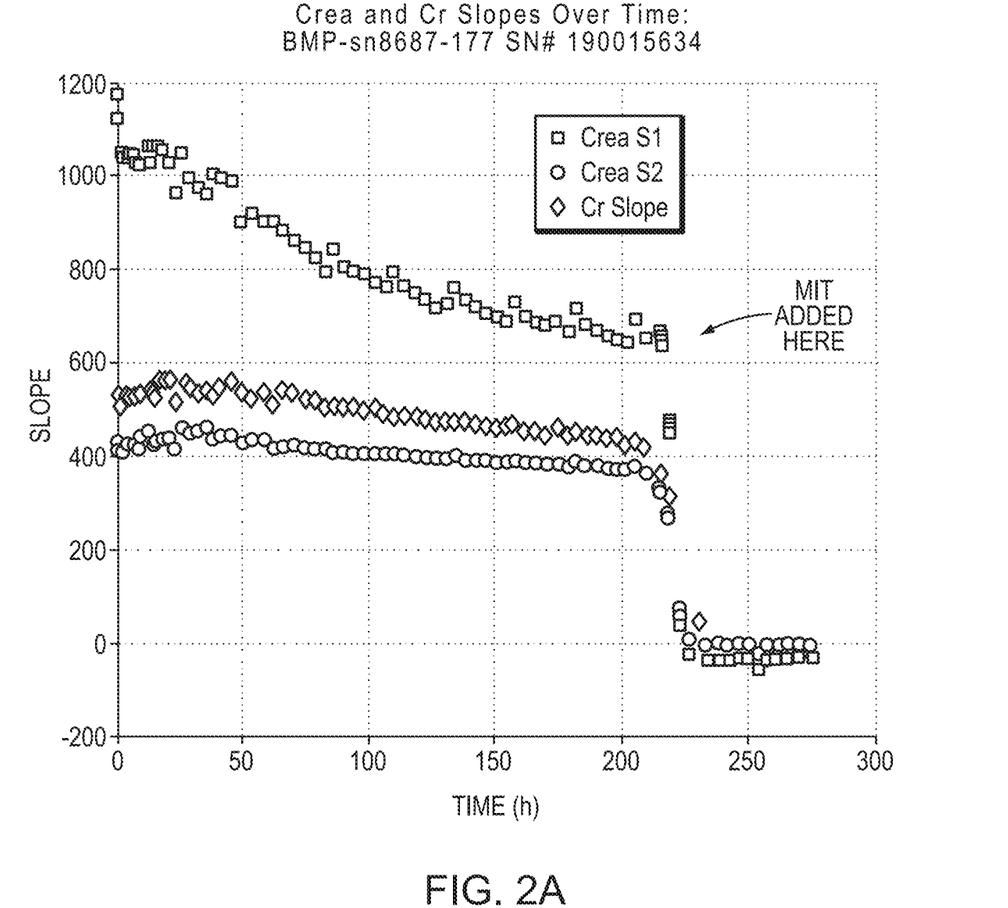
FIG. 2A shows a plot of creatinine and creatine slopes over time showing that addition of MIT causes a rapid decay in creatinine/creatine slopes that does not recover over time.

Most commonly used biocides inactivate creatine/creatinine biosensors. For example, a partial list of some of the antimicrobial agents that irreversibly inhibited creatininase, creatinase and sarcosine oxidase includes the following:

1. MIT (methyl isothiazolinone)
2. Cl-MIT (chlorinated methylisonthiazolinone)
3. BIT (benzylisothiazolinone)
4. MBIT (methylbenzisothiazolinone)
5. Norfloxacin
6. Trimethoprim
7. Omacide IPBC (iodopropynylbutylcarbamate)
8. Germall Plus
9. Dantogard Plus FIG. 2A shows a typical plot of creatinine and creatine slopes over time when MIT (methyl isothiazolinone) was added to PCS at 300 mg/L after establishing reasonably stable slopes (e.g., slope ≥400 for creatinine and ≥200 for creatine) for more than a week. The plot shows that adding MIT caused all three slopes to drop to zero in less than one day. MIT is the most common biocide used in the blood gas industry for microbial contamination, and is known to be compatible with oxidase class enzymes such as glucose oxidase and lactate oxidase. However, FIG. 2 clearly shows that hydrolase enzymes or sarcosine oxidase were more vulnerable to inhibition leading to the performance loss of creatinine sensor.

Figure 2B:
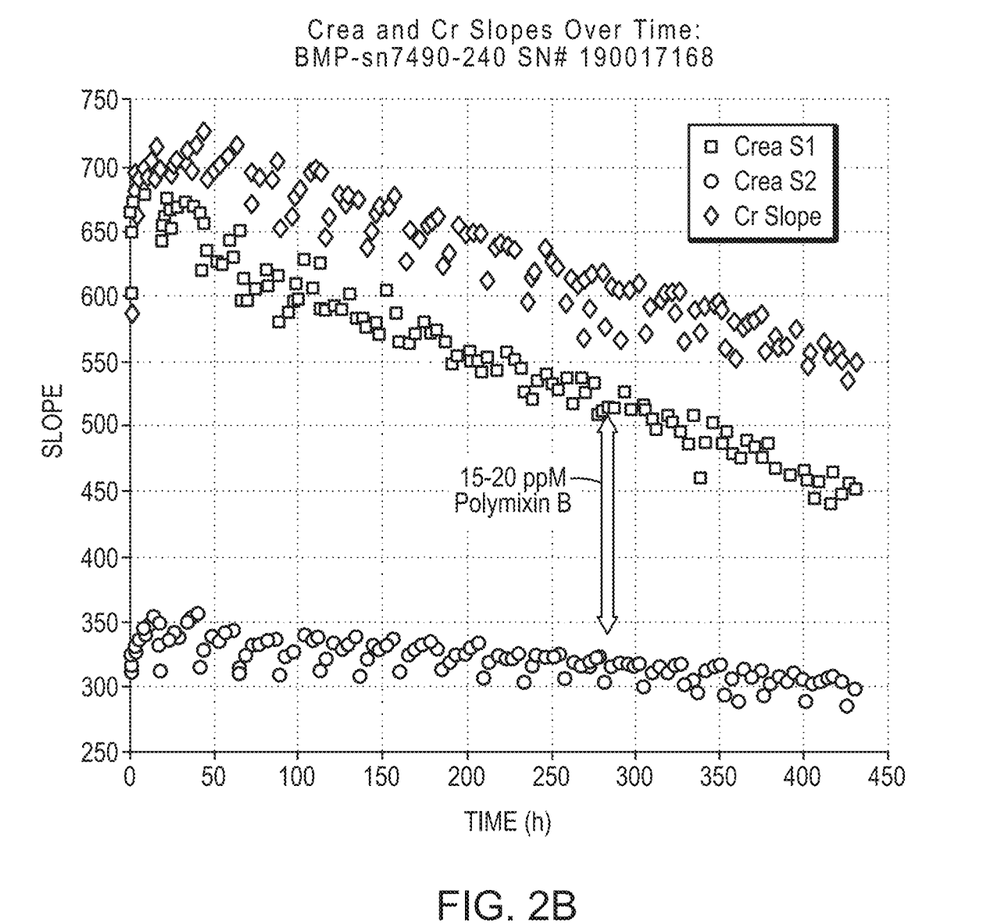
FIG. 2B shows a plot of creatinine and creatine slopes over time showing that addition of polymyxin B does not causes a rapid decay in creatinine/creatine slopes. Stable slopes were first established for more than one week before 300 mg/L MIT (methyl isothiazolinone) or 20 mg/L polymyxin B was added to the Process Control Solution (PCS) B (e.g., PCS-B).

In sharp contrast to MIT (above), the present disclosure found that Polymyxin B at 20 mg/L (below), for example, has no effect on creatinine or creatine slope (see e.g., FIG. 2B). Following this discovery, several additional rigorous tests were performed to confirm this unexpected enzyme compatibility as well as the efficacy of these two polymyxins in killing *Pseudomonas*.

Figure 3:
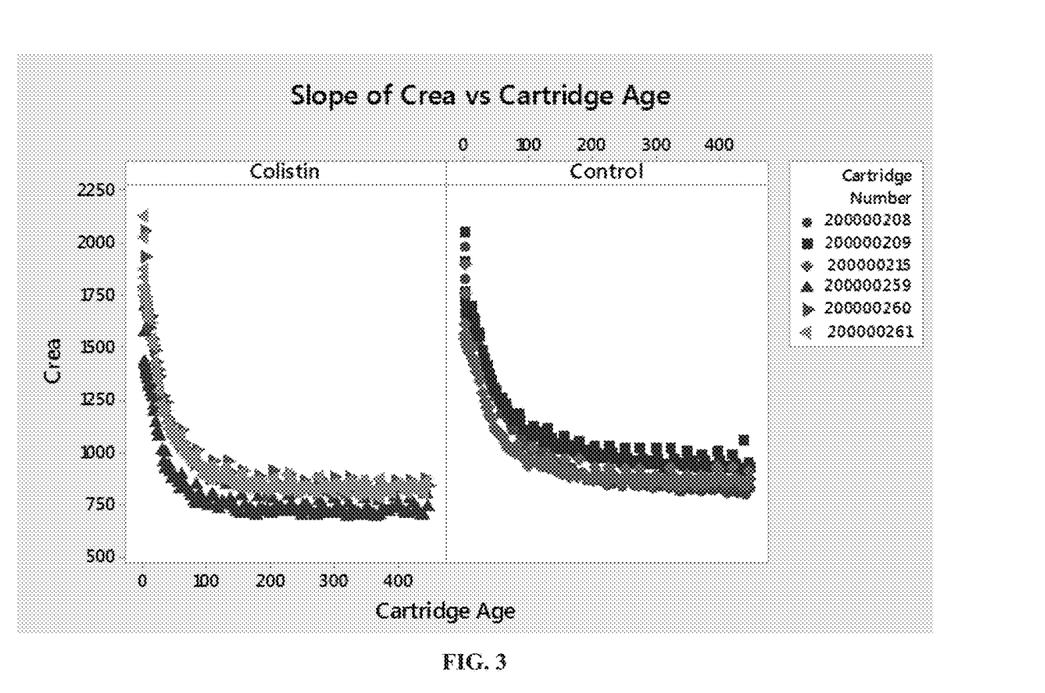
FIG. 3 shows example plots of creatinine slope performances over time in PCS with colistin (left) and gentamicin (right) showing that sensors maintained sufficient creatinine slope for a full use life of three weeks.

FIG. 3 shows example plots of creatinine slope performances over time in PCS with colistin (left) and gentamicin (right) showing that sensors maintained sufficient creatinine slope for a full use life of three weeks. Importantly, the creatinine slope performed equivalently with colistin in PCS bags (see FIG. 3, left) to cartridges with PCS bags protected only with gentamicin (see FIG. 3, right). In this plot, no bacterial contamination was observed on control or test biocide PCS bags nor was there any evidence of enzyme inhibition and therefore performance is similar.

Figure 4A:
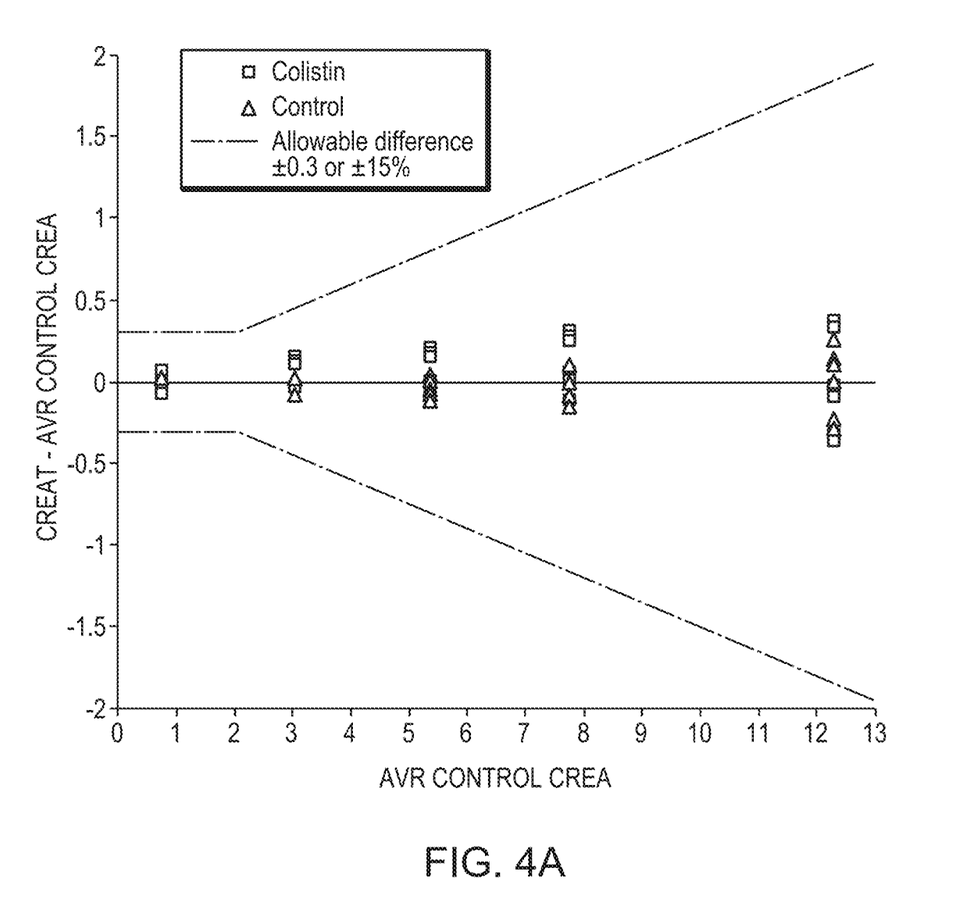
FIGS. 4A and 4B are graphs showing effects of colistin in the main calibration/wash solutions in either spiked blood samples (FIG. 4A) or clinical specimens (FIG. 4B).
Figure 4B:
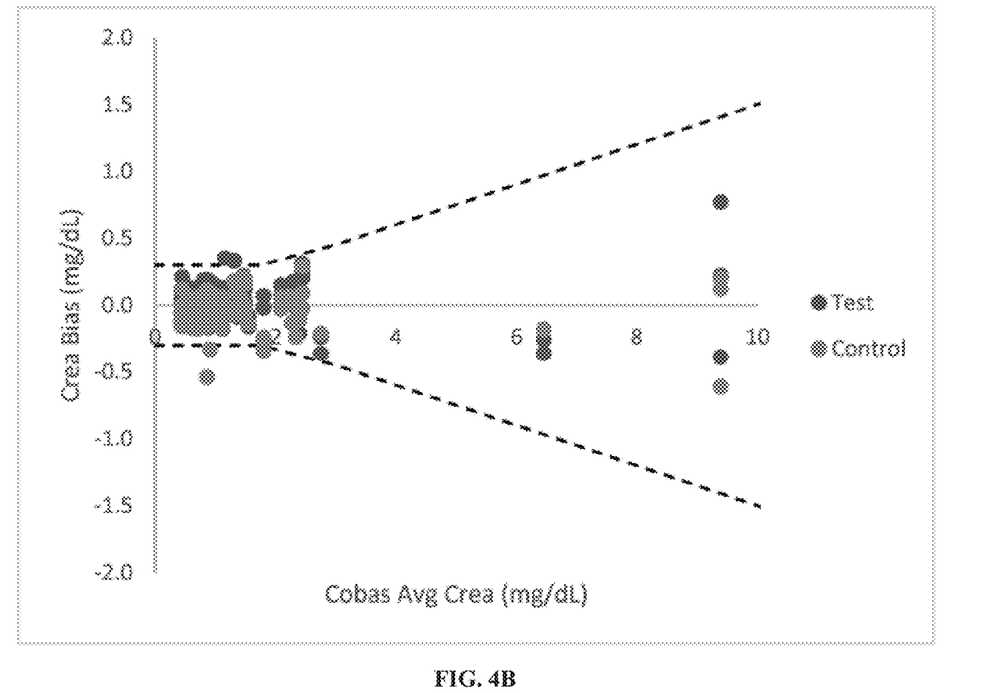

FIGS. 4A and 4B are graphs showing the effects of colistin spiked into the main calibration/wash solution(s) of either blood samples (FIG. 4A) or clinical specimens (FIG. 4B), which demonstrate excellent correlation to the above-described reference methods.

Example 2: Long Term Effect of Efficacious Biocides on Creatinine and Creatine Slopes Antimicrobial efficacy was established by independent assays, and the data is presented in Table 1 below. The B bag was protected with 40 mg/L colistin sulfate and 40 mg/L of amikacin, an aminoglycoside currently used in several GEM cartridge bags at 200 mg/L.

TABLE 1

ATCC 9027 *Pseudomonas aeruginosa* at an estimated inoculum size of 100,000 cfu/mL.

| Product | Day 1 CFU/ml | Day 3 CFU/ml | Day 7 CFU/ml | Day 14 CFU/ml |
|---|---|---|---|---|
| Rinse Solution | 20 | <1 | <1 | <1 |
| Blank | <1 | <1 | <1 | <1 |
| Plate Control | No Growth | No Growth | No Growth | No Growth |
| Pipette Control | No Growth | No Growth | No Growth | No Growth |
| Positive Control | Growth | Growth | Growth | Growth |

It can be seen that colistin caused rapid killing of *Pseudomonas*. Amikacin is normally used at 200 mg/L and is not known to be effective against gram negative rods at this lower concentration (40 mg/L).

An independent use life evaluation was performed using PCS bags spiked to 36 mg/L, and the results may be summarized as follows:

For the 3 week use-life
- All 3 cartridges for 12 analytes (pH, $pCO_2$, $Na^+$, $K^+$, $Ca^{++}$, $Cl^-$, Glucose, Lactate, Creatinine, BUN, $tCO_2$, and Hct) had passed calibration verification and there were no detected intelligent quality management errors
- all slopes and drifts, including Creatinine and Creatine, behaved normally
- Glucose in high glucose low oxygen aqueous showed no decrease in recovery (indicating no loss of $pO_2$): Glu ≥384 mg/dL on all 3 cartridges vs lower limit ~350 mg/dL.
- Linearity was good for all enzyme sensors (Crea, BUN, Glu, Lac) based on aqueous controls levels 1-5
- $pO_2$ was normal for 3 cartridges;
- Blood Panel performance for weeks 1, 2 & 3 met performance requirements per the total allowable error limits published in the instrument manual.
- Overall, Polymyxin E (40 ppm) spiked PCS bags showed no harm to any sensors.

As described herein, an unusual class of antibiotics were discovered that were capable of killing *Pseudomonas*, which were resistant to Gentamicin, without inhibiting the activity of the hydrolase enzymes used in the outer membrane of the creatinine sensor on the ChemSTAT sensor card.

Example 3: Methods of Screening Compounds for Enzyme Compatible Biocides

According to the techniques herein, enzyme compatible biocides may be identified in a variety of ways.

In one embodiment, a biocide candidate may be injected into, for example, one PCS-B bag after about one week of cartridge use life, and then any changes in sensor slopes over the next week or two, especially any increase in the rate of slope decrease, may be observed. During this time, aqueous solutions with high substrate concentrations may be tested to ensure that enzymes are still able to convert all substrate to products in the allotted time (e.g., about one minute).

In one embodiment, multiple cartridges assembled with, for example, PCS-B bags containing a candidate biocide may be tested for a prolonged period of time (e.g., 20-30 days) that corresponds to the useful cartridge lifespan (which may vary depending upon the cartridge type tested). In this case the cartridge starts the hydration process, which generally lasts about 50 minutes, with the biocide already in the solution bag (e.g., PCS-B). At least 3 cartridges may generally be tested, and a control cartridge(s) that does not contain the test substance in the solution bag (e.g., PCS-B) may also be included. Over the course of 3 weeks, in addition to running aqueous controls that have established acceptance ranges, whole human blood may also be tested in order to simulate normal customer use. At the end of the test period the slope pattern for all sensors (enzyme biosensors, ion selective sensors, gas sensors and physical sensors such as conductivity sensors) is examined to ensure that they remain within pre-established performance limits and that they do not exhibit excessive electronic drift.

Example 4: Identification of Biocides Compatible with the Creatinine Sensor

A variety of candidate molecules were screened as described above to determine whether they were compatible with the Creatinine Sensor, i.e. whether there was a significant effect on Creatinine Sensor Slope. Table 2 lists compounds vs compatibility, molecular weight (MW) in g/mol, and molecular structure. "Fail" indicates the compound inhibited Creatinine Sensor Slope, whereas "Pass" indicates there was no significant effect on Creatinine Sensor Slope.

TABLE 2

Summary of Biocide/Antibiotic MW & Structure vs Creatinine Sensor Slope Loss

| Compound | Pass/Fail | MW | Structure |
| --- | --- | --- | --- |
| MIT (methyl isothiazolinone) | Fail | 115 | |
| Dantogard Plus (dimethylhydantoin) | Fail | 128 | |
| 8-hydroxyquinoline | Fail | ~145 | |
| Cl-MIT (chlorinatedmethyl-isonthiazolinone) | Fail | 150 | |
| BIT (benisothiazolinone | Fail | 151 | |
| MBIT (methylbenziso-thiazolinone) | Fail | 165 | Similar to BIT |
| 2-phenyl phenol | Fail | ~170 | |
| Omacide IPBC (iodopropynylbutylcarbamate) | Fail | 281 | |

TABLE 2-continued

Summary of Biocide/Antibiotic MW & Structure vs Creatinine Sensor Slope Loss

| Compound | Pass/Fail | MW | Structure |
| --- | --- | --- | --- |
| Germall Plus (diazolidinyl urea + IPBC) | Fail | 278 |  |
| Trimethoprim (lactate) | Fail | 290 |  |
| Norfloxacin | Fail | 319 |  |
| Levofloxacin | Pass | 361 |  |
| Carbenicillin disodium | Pass | 378 |  |
| Gentamicin sulfate | Pass | ~464 |  |

TABLE 2-continued

Summary of Biocide/Antibiotic MW & Structure vs Creatinine Sensor Slope Loss

| Compound | Pass/Fail | MW | Structure |
|---|---|---|---|
| Spectinomycin | Pass | 495 | |
| Piperacillin | Pass | 539 | |
| Ceftazidime | Pass | 546 | |
| Amikacin sulfate | Pass | 586 | |

TABLE 2-continued

Summary of Biocide/Antibiotic MW & Structure vs Creatinine Sensor Slope Loss

| Compound | Pass/Fail | MW | Structure |
|---|---|---|---|
| Streptomycin | Pass | 728 |  |
| Polymyxin B | Pass | 1190 | See below |
| Polymyxin E (colistin sulfate) | Pass | 1190 | See below |
| Vantocil ™ IB (Cosmocil CQ) (PHMB HCl) | Pass | 2200 |  n = 12 |

Polymyxin E (Colistin)

Polymyxin B

The above data shows that biocidal reagents with a molecular weight (MW) greater than 320 do not inhibit or prevent enzymatic biosensor function. Exemplary efficacious biocidal reagents that do not inhibit or prevent the function of enzymatic biosensors include, but are not limited to, Levofloxacin, Carbenicillin disodium, Spectinomycin, Piperacillin, Ceftazidime, Streptomycin, Polymyxin B, Polymyxin E, Sulfanilamide, Sulfathiazole sodium, Sulfadimethoxine, Vantocil™ IB, and the like.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

EQUIVALENTS

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A composition comprising:
   enzyme compatible biocides, the enzyme compatible biocides comprising (i) Levofloxacin and (ii) Polymyxin, where the Polymyxin comprises Polymyxin B or Polymyxin E (Colistin);
   creatininase;
   creatinase; and
   sarcosine oxidase.

2. A composition comprising:
   an enzyme compatible biocide comprising Polymyxin;
   creatininase;
   creatinase; and
   sarcosine oxidase.

3. A system comprising:
   a sensor comprising the composition of claim 2 for measuring a concentration of one or more analytes.

4. The system of claim 3, wherein the sensor comprises an enzyme biosensor.

5. The system of claim 4, wherein the enzyme biosensor comprises a creatinine sensor, a creatine sensor, or a combination thereof.

6. The system of claim 3, further comprising an enzyme compatible biocide having a molecular weight greater than about 320 g/mol.

7. The system of claim 3, wherein the Polymyxin comprises Polymyxin B, Polymyxin E, or a combination thereof.

8. The system of claim 3, wherein the Polymyxin comprises Polymyxin B.

9. The system of claim 3, wherein the composition comprises a fluoroquinolone antibiotic.

10. The system of claim 3, further comprising a Beta-lactam antibiotic, the Beta-lactam antibiotic comprising amoxycillin, ampicillin, carbenicillin, cefazolin, cefepime, cefoxitin, ceftazidime, clavulanic acid, imipenem, oxacillin, penicillin, or piperacillin.

11. The system of claim 3, further comprising at least one fluoroquinolone antibiotic.

12. The composition of claim 2, further comprising at least one of Levofloxacin, Carbenicillin disodium, Spectinomycin, Piperacillin, Ceftazidime, Streptomycin, Sulfanilamide, Sulfathiazole sodium, Sulfadimethoxine, or polyhexamethylene biguanide hydrochloride.

13. The composition of claim 2, wherein the Polymyxin comprises Polymyxin B and Polymyxin E.

14. The composition of claim 2, further comprising penicillin comprising amoxycillin or benzyl penicillin.

15. The composition of claim 14, where the penicillin is at a concentration of about 12.5 to about 500 µg/ml.

16. The composition of claim 2, further comprising carbenicillin at a concentration of about 5 to about 800 µg/mL or an aminoglycoside at a concentration of about 20 to about 800 µg/mL.

17. The composition of claim 2, further comprising about 15 to about 500 mg/L spectinomycin.

18. The composition of claim 2, further comprising about 10 to about 500 mg/L of ceftazidime.

19. The composition of claim 2, further comprising about 10-500 mg/L streptomycin.

20. The composition of claim 2, wherein the Polymyxin is Polymyxin B.

21. The composition of claim 2, wherein the Polymyxin is Polymyxin E.

22. The composition of claim 2, further comprising polyhexamethylene biguanide hydrochloride in a w/v of 0.1 to 0.5% in aqueous solution.

23. The composition of claim 2, further comprising a fluoroquinolone antibiotic.

24. The composition of claim 2, wherein the Polymyxin comprises Polymyxin E or Polymyxin B at a concentration of about 20 to 100 mg/L.

25. The composition of claim 2, wherein the Polymyxin is at a concentration of about 20 to 100 mg/L.

26. A method comprising:
    measuring a concentration of one or more analytes using a sensor comprising the composition of claim 2.

27. The method of claim 26, wherein the sensor is part of a system, the system comprising a cartridge for an analyzer system.

28. The method of claim 26, wherein the sensor comprises an enzyme biosensor.

29. The method of claim 28, wherein the enzyme biosensor comprises a creatinine sensor, a creatine sensor, or a combination thereof.

* * * * *